United States Patent
Scott

(10) Patent No.: US 7,018,663 B2
(45) Date of Patent: Mar. 28, 2006

(54) APPLICATION OF DRIED NETTLE TO THE SKIN

(75) Inventor: Donald E. Scott, 1630 Old Rushville Rd., Rushville, OH (US) 43150

(73) Assignee: Donald E. Scott, Rushville, OH (US)

( * ) Notice: Subject to any disclaimer, the term of this patent is extended or adjusted under 35 U.S.C. 154(b) by 134 days.

(21) Appl. No.: 10/301,336

(22) Filed: Nov. 21, 2002

(65) Prior Publication Data

US 2005/0249830 A1 Nov. 10, 2005

(51) Int. Cl.
*A61K 35/78* (2006.01)
*A61L 15/16* (2006.01)

(52) U.S. Cl. ............... 424/725; 424/773; 424/774; 424/776; 424/779; 424/446; 424/447

(58) Field of Classification Search ............... 424/725, 424/774, 773, 776, 779, 446, 447
See application file for complete search history.

(56) References Cited

U.S. PATENT DOCUMENTS

| | | | |
|---|---|---|---|
| 4,258,035 A | 3/1981 | Spies | 424/195 |
| 4,886,665 A | 12/1989 | Kovacs | 424/195.1 |
| 5,683,698 A | 11/1997 | Chavali et al. | 424/195.1 |
| 5,854,291 A | 12/1998 | Laughlin et al. | 514/626 |
| 5,856,361 A | 1/1999 | Holt et al. | 514/627 |
| 5,869,533 A | 2/1999 | Holt | 514/627 |
| 5,916,565 A | 6/1999 | Rose et al. | 424/195.1 |
| 5,997,876 A * | 12/1999 | Shikhashvili et al. | |
| 6,060,062 A | 5/2000 | Fowler | 424/195.1 |
| 6,113,926 A | 9/2000 | Soler et al. | 424/401 |
| 6,241,987 B1 | 6/2001 | Lam | 424/195.1 |
| 6,333,056 B1 | 12/2001 | Robinson | 424/725 |
| 6,352,728 B1 * | 3/2002 | Butters et al. | 424/776 |
| 6,579,543 B1 * | 6/2003 | McClung | 424/728 |
| 2002/0022052 A1 * | 2/2002 | Dransfield | 424/449 |
| 2002/0034555 A1 * | 3/2002 | Gelber et al. | 424/725 |
| 2002/0064568 A1 | 5/2002 | Rose et al. | |
| 2004/0208943 A1 * | 10/2004 | Miketin | 424/730 |

FOREIGN PATENT DOCUMENTS

| | | | |
|---|---|---|---|
| FR | 2812 | * | 6/1966 |
| JP | 07101836 | * | 4/1995 |
| RU | 2214818 | * | 10/2003 |
| WO | WO 01/95727 | | 12/2001 |
| WO | WO 02/04003 | | 1/2002 |
| ZA | 200000857 | * | 8/2001 |

OTHER PUBLICATIONS

Muravev et al. Development of a Technology for a Preparation of Tatal Water-Soluble Substances from *Urtica dioica*. Farmatsiya (Moscow). 1986. vol. 35, No. 6, pp. 17-20, DRUGU Abstract enclosed.*

Randall, *Randomized controlled trial of nettle sting for treatment of base-of-thumb pain*, JR Soc Med. 2000: 93(6):305-309.

Randall, *Nettle Sting of Urtica Dioica for joint pain—an exploratory study of this complementary therapy*, Comp. Ther. Med 1999;7:125-131.

Obertreis B., et al., *Anti-inflammatory effect of Urtica dioica folia extract in comparison to caffeic malic acid*, Scientific article, Arzneimittelforschung Jan. 1996;46(1):52-6.

Karin Granstrom Jordan, M.D., *Osteoarthritis and Rheumatoid Arthritis*, Scientific Article, www.lef.org., Date Unknown.

Susie Sparks, *Superb Herb—Stinging Nettles*, Internet article, www.mtnmedical.com, Date unknown.

Robin E. Langer, R.Ph., *Stinging Nettle (Urtica dioica)*, Internet article, www.sbherbals.com, Dec., 1999.

Unknown, *ArthroPro—commercially available Nettle as oral dietary supplement*, Internet website, www.lef.org., Date unknown.

Euell Gibbons, *The Common Stinging Nettle*, Internet article, www.ruralvermont.com, Excerpted from Stalking the Healthful Herbs, Date unknown.

Michael McRae, *I Am Monkey Flower*, Internet article, www.outsidemag.com, Jul., 1997.

Mrs. M. Grieve, *A Modern Herbal—The Medicinal, Culinary, Cosmetic and Economic Properties, Cultivation and Folk-Lore of Herbs, Grasses, Fungi, Shrubs & Trees with All Their Modern Scientific Uses*, vol. II, Dover Publications, Inc., (1971), pp. 574-582.

* cited by examiner

*Primary Examiner*—Christopher R. Tate
(74) *Attorney, Agent, or Firm*—Wood, Herron & Evans, LLP

(57) ABSTRACT

The invention is directed to a composition and method in which dried stinging nettle is applied to the skin proximate a pain site to alleviate pain associated with various inflammatory conditions. The characteristic sting of the stinging nettle is absent in the dried nettle of the composition and method.

12 Claims, No Drawings

APPLICATION OF DRIED NETTLE TO THE SKIN

BACKGROUND OF THE INVENTION

1. Field of the Invention

The present invention pertains generally to a composition and method for alleviating pain and, more particularly, to a composition and method in which dried stinging nettle is applied to the skin proximate a pain site to alleviate pain associated with various inflammatory conditions.

2. Description of the Related Art

Many modern medications have been developed from ancient healing traditions associated with specific plants. The medicinal properties of plants have been identified with specific chemical compounds which have been isolated, purified and, in many cases, synthetically reproduced. Many well-known drugs were originally derived from plants. For example, salicylic acid, the precursor for aspirin, was originally isolated from white willow bark and the meadowsweet plant. Quinine, which is used to treat malaria, was derived from Cinchona bark. Morphine, derived from the opium poppy, is still the standard against which new synthetic pain relief drugs are measured.

Modern physicians tend to rely on treatments using synthetic or chemically-manufactured drugs. Rather than using whole plants or plant extracts for treatment, pharmacologists tend to identify, isolate, extract, insulate, and synthesize the active compounds from plants for use in treatment. This approach, however, has drawbacks. In addition to the individual physiologically active compounds present in a plant, there are also minerals, vitamins, oils, alkaloids, and other substances which can be important in supporting the medicinal properties of a particular plant. These additional substances can provide a synergistic effect which is absent when purified or synthetic active compounds are used alone.

Various new and old drugs, from aspirin to non-steroidal anti-inflammatory drugs (NSAIDs) to cortisone, have been developed for the treatment of pain associated with inflammation. Musculoskeletal pain, commonly caused by inflammation following injury, is a common reason for self-treatment and/or consultation with a physician. Drugs such as aspirin or NSAIDs are the most common treatment. Arthritis is a general term for a disease involving inflammation of a joint or joints, and encompasses more than one hundred different diseases, frequently having entirely different causes. Osteoarthritis and rheumatoid arthritis, the two most common forms of arthritis, have the greatest public health implications. Osteoarthritis, also known as "degenerative joint disease" or "wear and tear" arthritis, results from physical changes in joints and surrounding tissues, leading to pain, tenderness, swelling, and decreased function. The joints most often affected are the hip, knee, and hand. Rheumatoid arthritis is an autoimmune inflammatory disease of the whole body, characterized by chronic inflammation of the joint linings, not of the joints alone, and in particular the connective tissues of the body.

In both types of arthritis many manifestations are similar. The joints, whether singly or in multiples, may become swollen, warm, deformed, gnarled, and in many instances present grotesque deformities. In many cases the adjacent muscles and tendons are affected, as well as other connective tissues of the body, manifested by symptomatic swelling, pain and stiffness. Likewise, musculoskeletal pain, such as pulled muscles and broken bones, and hemorrhoids are characterized by symptomatic inflammation, swelling and pain.

The enormous consumption of painkillers and anti-inflammatory drugs to treat inflammatory conditions such as arthritis, musculoskeletal pain, and hemorrhoids often has undesirable long-term effects, and many of these systemic drugs have dangerous side effects. Their dosage must be carefully prescribed and administered under controlled conditions and circumstances.

As an alternative to modern anti-inflammatory drugs, the sting of the common stinging nettle has been used to treat inflammation and arthritic pain. Stinging nettle (*Urtica dioica, Urtica urens*) is a perennial, slow-spreading plant that grows from 2 to 9 feet tall. The leaves are coarsely-toothed, with numerous, small bristly stinging hairs over much of their surface. The undersides of the nettle leaves and stems have small needle-like structures. Stinging nettle is a native species throughout Europe, Asia, Africa, Australia, and the Andes Mountains in South America, as well as in North America. It is confined primarily to shaded, moist areas along streams, or in deep, rich undisturbed soils. Also difficult to eradicate, it is primarily a nuisance to recreationists because of its stinging hairs, which are indeed quite painful to the touch.

The Romans in ancient times used the sting of stinging nettle to alleviate joint and muscle pain by urtication (external stinging or flogging). They also did this to keep warm in the winter. Reports have also been found of nettle urtication for the treatment of arthritic pain by the Thompson Indians in Vancouver Island, British Columbia, throughout the British Isles, and in the United States. *Nettle Sting of Urtica Dioica for joint pain—an exploratory study of this complementary therapy*, Randall C, Meethan K, Randall H, Dobbs f. Comp. Ther. Med 1999;7:125–131. Research by Dr. Colin Randall at the University of Plymouth, U.K. also reports the use of the sting of the common stinging nettle to treat the pain of osteoarthritis and musculoskeletal pain. *Randomized controlled trial of nettle sting for treatment of base-of-thumb pain*, Randall C, Randall H, Dobbs F, Hutton C, Sanders H. J R Soc Med. 2000: 93(6):305–309.

While stinging nettle are known for alleviating arthritis pain with their sting, it is also known that a particular nettle extract can relieve the pain of skin burning and irritation. U.S. Pat. Nos. 5,854,291 and 5,856,361 by Holt and Laughlin, entitled "Pain Reliever and Method of Use," disclose a topically-applied capsaicin-based pain reliever for inflammatory conditions in which an ingredient is required to relieve the side-effect of skin burning and irritation caused by capsaicin. This ingredient is selected from either a polyol, a nettle extract, a yarrow extract, a coltsfoot extract, a birch extract, a rosemary extract, a horsetail extract, a ginger extract, a chamomile extract, a comfrey extract, a lavender extract, or a bergamot extract.

Also, the oral ingestion of nettle for the systemic treatment of arthritis is known. Rose et al., in U.S. Pat. Nos. 5,916,565 and 6,344,220, entitled "Product and Method for Treating Joint Disorders in Vertebrates," disclose an orally-administered composition including metabolic precursors, herbal phytochemicals, and palatability agents capable of prophylaxis and therapy of joint and connective tissue disorders in vertebrates. The composition is primarily intended for ingestion by dogs, horses, and cats. The herbal phytochemicals are intended to provide a synergistic effect with the metabolic precursors glucosamine and chondroitin sulfate, and include cayenne, ginger, turmeric, yucca, Devil's claw, nettle leaf, Black Cohosh, alfalfa and celery seeds.

While the above uses of nettle may be sufficient for their specific, intended purposes, they each have disadvantages. Accordingly, there remains a substantial need for an effective externally-applied treatment for pain associated with arthritis and other forms of inflammatory disease. There is also a need for such a treatment whereby stinging nettle can be applied to the skin without causing a sting, pain, or rash.

SUMMARY OF THE INVENTION

Accordingly, it is an object of the present invention to provide an alternative methodology for effectively relieving or inhibiting the pain associated with inflammatory conditions such as arthritic inflammation, musculoskeletal inflammation, and/or hemorrhoids. Another objective of the present invention is to provide a method for applying dried nettle to a pain site. It is another objective to provide a composition including dried stinging nettle, preferably processed in the form of a powder or flakes, in which the nettle no longer causes a sting or rash when applied. It is a further objective to provide a method of processing dried stinging nettle for use in pain relief from inflammation.

To this end, a method of alleviating or inhibiting pain associated with inflammation according to the present invention includes the step of applying dried stinging nettle to the skin proximate a pain site. The inflammation may be caused by various physical injuries or conditions, such as, for example, osteoarthritic inflammation, musculoskeletal inflammation, and hemorrhoids. The method described herein is extremely advantageous since, according to a preferred embodiment of the invention, no other medications need be combined with the nettle to alleviate the pain.

As a non-limiting example of how the invention is used in practice, a person experiencing pain from inflammation may take a dried nettle plant, or preferably a small amount of a dry mixture of component parts thereof, such as a powder comprised of dried nettle leaves and/or buds, and apply the nettle directly to the skin overlying the painful area. Preferably the applied nettle is then temporarily secured in place after application by a bandage or the like, preferably for a period of at least about 12 hours, and more preferably for at least about 72 hours. Thereafter the nettle is removed and the person may enjoy relief from the pain.

A further understanding of the nature and advantages of the present invention will become apparent when taken together with the remaining portions of the specification.

DETAILED DESCRIPTION OF SPECIFIC ASPECTS OF THE INVENTION

Definitions: The following terms used herein are intended to have the following meanings:

Cellular integrity as it applies to stinging nettle is defined as the microscopic, cellular makeup being intact, unimpaired and/or free from injury. Actions such as freezing, pulverizing or crushing may destroy cellular integrity.

Component part is defined as any one or more of bud, leaf, stem (stalk), root, and seed of a stinging nettle plant. The terms bud, leaf, stem, root, and seed can mean either the singular or the plural.

Dried or Drying is defined as the physical state of a harvested stinging nettle plant in which the plant no longer has the ability to cause the notoriously painful sting associated with stinging nettle, due to the plant becoming wizened, shriveled, wrinkled and/or shrunken as a result of a loss of natural moisture and vitality.

Harvested as it relates to a nettle plant is defined as gathered, removed, or extracted from a growing medium, such as the ground or another portion of the plant.

Inflammation is defined as a local response to a physiological condition which typically results in pain, and may be accompanied by redness, swelling and/or heat.

Maturity or mature as it relates to stinging nettle is defined as that which has been allowed to grow long after blossoming, and has been harvested as late into the fall season as possible, before a freeze.

Milling as it relates to processing of stinging nettle is defined as mixing and mingling, preferably manually, of one or more component parts of a dried nettle plant or plants without destroying the cellular integrity of the component part(s).

Nettle is defined as a plant, multiple plants, and/or one or more portions of the plant(s) belonging to a strain of stinging nettle. The particular strain of stinging nettle plant includes, but is not limited to, the family *Urtica dioica* and *Urtica urens*. *Urtica dioica*, also known as *Urtica gracilis*, is a perennial plant with slender leaves that grows up to 5–10 feet tall. *Urtica urens* is a greener, smaller variety of stinging nettle with broader leaves, and grows up to 3–8 feet tall.

Pain site is defined as the area or location on the body of an individual experiencing pain associated with inflammation.

Portion is defined as any part of the nettle plant, ranging from a small part of one of the component parts to the entire plant.

The invention is directed to a method to alleviate pain associated with various conditions such as, for example, osteoarthritic inflammation, musculoskeletal inflammation, and hemorrhoids. The method includes the application of dried nettle, preferably in the form of a powder or flakes, to the skin overlying a pain site. Preferably the powder and/or flakes are exclusively a combination of the leaves and buds of the plant, but other component parts such as the seeds or stems may be applied as well. However, no other medications need be combined with the nettle. The nettle may be kept in place by a bandage or the like, preferably for a period of at least about 12 hours, and more preferably for at least about 72 hours. While not being bound by theory, it is believed that, when used in this manner, the applied dried nettle reduces swelling and inflammation associated with pain, and does so for a relatively long period of time, as compared to aspirin, NSAIDs, steroid injections, or other conventional medications or treatments.

While not being bound by theory, it is believed to be advantageous to grow the stinging nettle plant long after blossom (stinging nettle typically blossom in mid-summer) before harvesting in late fall, before a freeze. This is because the mature plant may be more potent and have a longer duration of action. The plant may then be harvested by cutting at the base of the stalk, pulling by the root, or the like. It also is believed that drying of the harvested plant thereafter causes it to lose its sting. One method of drying may include hanging the plant upside down in a well-ventilated area, such as a barn. Further, it is believed that hanging in this manner may allow one or more active ingredients which may be in the stalk and/or roots to move into the leaves and/or buds.

After drying, the nettle plant is preferably milled in order to convert, break apart, separate and/or reduce the nettle plant into its component parts. Also, it is preferable to continue to mill the component parts prior to application, preferably until they are in the form of flakes, and more preferably a fine powder. Since it is preferred to apply mainly leaf and bud only over the pain site, it is also preferable to separate out and remove the stems and seeds from the milled component parts. Additionally, it is preferable that large lots of nettle plants are combined prior to the milling step to assure consistency in the potency of the batch.

While not being bound by theory, it is believed to be advantageous to treat the nettle plant in a manner that does not freeze, crush, damage or lyse the cells, or otherwise destroy cellular integrity. This is because the active substance or substances responsible for the pain alleviating effects are believed to be found only in intact cells. In addition, it is believed that these active substance(s) are more potent and have a longer duration of action in the mature plant. Therefore, it may be important during processing of the harvested nettle plant that actions such as freezing or pulverizing not be done, because this may destroy the cellular integrity of the component parts, especially the leaves and buds.

It is to be understood that the above description is intended to be illustrative and not restrictive. Many embodiments may become apparent to those of ordinary skill in the art upon reviewing the above description. By way of example, the invention has been described primarily with reference to the use of bandages or wraps to keep the nettle in place. However, it may be readily recognized that other items could be used to maintain the nettle in contact with the skin. The scope of the invention should, therefore, be determined not with reference to the above description, but instead be determined with reference to the appended claims, along with the full scope of equivalents to which such claims are entitled.

What is claimed is:

1. A method of alleviating or inhibiting pain associated with inflammation relating to arthritis, musculoskeletal injury, or hemorrhoids in a mammal, comprising the step of:
    applying a portion of a dried stinging nettle plant to an area of the skin of the mammal proximate a pain site.

2. The method of claim 1, wherein the portion is selected from the group consisting of bud, leaf, stem, root seed, and combinations thereof.

3. The method of claim 1, wherein the portion consists essentially of bud and leaf.

4. The method of claim 1, wherein the dried stinging nettle plant is selected from the group consisting of *Urtica dioica, Urtica urens*, and combinations thereof.

5. The method of claim 1, further including releasably securing the portion over the pain site.

6. The method of claim 5, wherein the portion is secured for at least about 12 hours.

7. The method of claim 5, wherein the portion is secured for at least about 72 hours.

8. The method of daim 1, wherein the arthritis is located at a pain site selected from the group consisting of a knee joint, an elbow joint, a shoulder, the spinal column, and combinations thereof.

9. The method of claim 1, wherein the musculoskeletal injury is located at a pain site selected from the group consisting of a knee joint, a rotator cuff, an elbow joint, a broken bone, and combinations thereof.

10. A method of alleviating or inhibiting pain associated with inflammation relating to arthritis, musculoskeletal injury, or hemorrhoids in a mammal, the method comprising the steps of:
    applying a portion of dried stinging nettle plant to an area of the skin of the mammal proximate a pain site;
    releasably securing the portion to the area; and
    maintaining the portion on the area for a period of time.

11. The method of claim 10, wherein the period has a duration which is predetermined.

12. The method of claim 11, wherein the duration is between about 12 hours and about 72 hours.

* * * * *

UNITED STATES PATENT AND TRADEMARK OFFICE
CERTIFICATE OF CORRECTION

PATENT NO. : 7,018,663 B2 Page 1 of 1
APPLICATION NO. : 10/301336
DATED : March 28, 2006
INVENTOR(S) : Donald E. Scott It is certified that error appears in the above-identified patent and that said Letters Patent is hereby corrected as shown below:

Column 2,
Line 32, "f." should be -- F. --.

Column 6,
Line 14, "daim" should be -- claim --.

Signed and Sealed this

Fifteenth Day of August, 2006

JON W. DUDAS
*Director of the United States Patent and Trademark Office*